United States Patent [19]
Hergeth

[11] Patent Number: 5,626,237
[45] Date of Patent: May 6, 1997

[54] PROCESS FOR THE RAPID RECOGNITION AND FILTERING OUT OF DIFFERENTLY COLORED FOREIGN BODIES IN FIBER PROCESSING LINES

[76] Inventor: Hubert A. Hergeth, Konigsmuhlenweg 11, 52076 Aachen, Germany

[21] Appl. No.: 344,822

[22] Filed: Nov. 23, 1994

[30] Foreign Application Priority Data

Nov. 25, 1993 [DE] Germany ............... 43 40 165.1

[51] Int. Cl.⁶ ............... B07C 5/342; G01J 3/50
[52] U.S. Cl. ............ 209/580; 209/644; 356/402; 356/407
[58] Field of Search ................... 356/402, 407; 209/580, 644; 348/88, 125, 129

[56] References Cited

U.S. PATENT DOCUMENTS

| | | | |
|---|---|---|---|
| 5,058,444 | 10/1991 | Anthony et al. | 73/866 |
| 5,087,120 | 2/1992 | Anthony | 356/36 |
| 5,125,279 | 6/1992 | Anthony et al. | 73/866 |
| 5,383,135 | 1/1995 | Shofner et al. | 364/552 |

*Primary Examiner*—F. L. Evans
*Attorney, Agent, or Firm*—Lockwood, Alex, FitzGibbon & Cummings

[57] ABSTRACT

The invention relates to a process which enables foreign bodies to be rapidly recognized and filtered out of fibre processing lines. A stream of fibres is inspected by color sensors. If foreign bodies are detected in the flow of fibres, they are blown out by compressed air nozzles (13). The inspection and filtering out can be performed with continuous operation, and purposeful filtering out blows only a few foreign bodies out with the fibres.

13 Claims, 1 Drawing Sheet

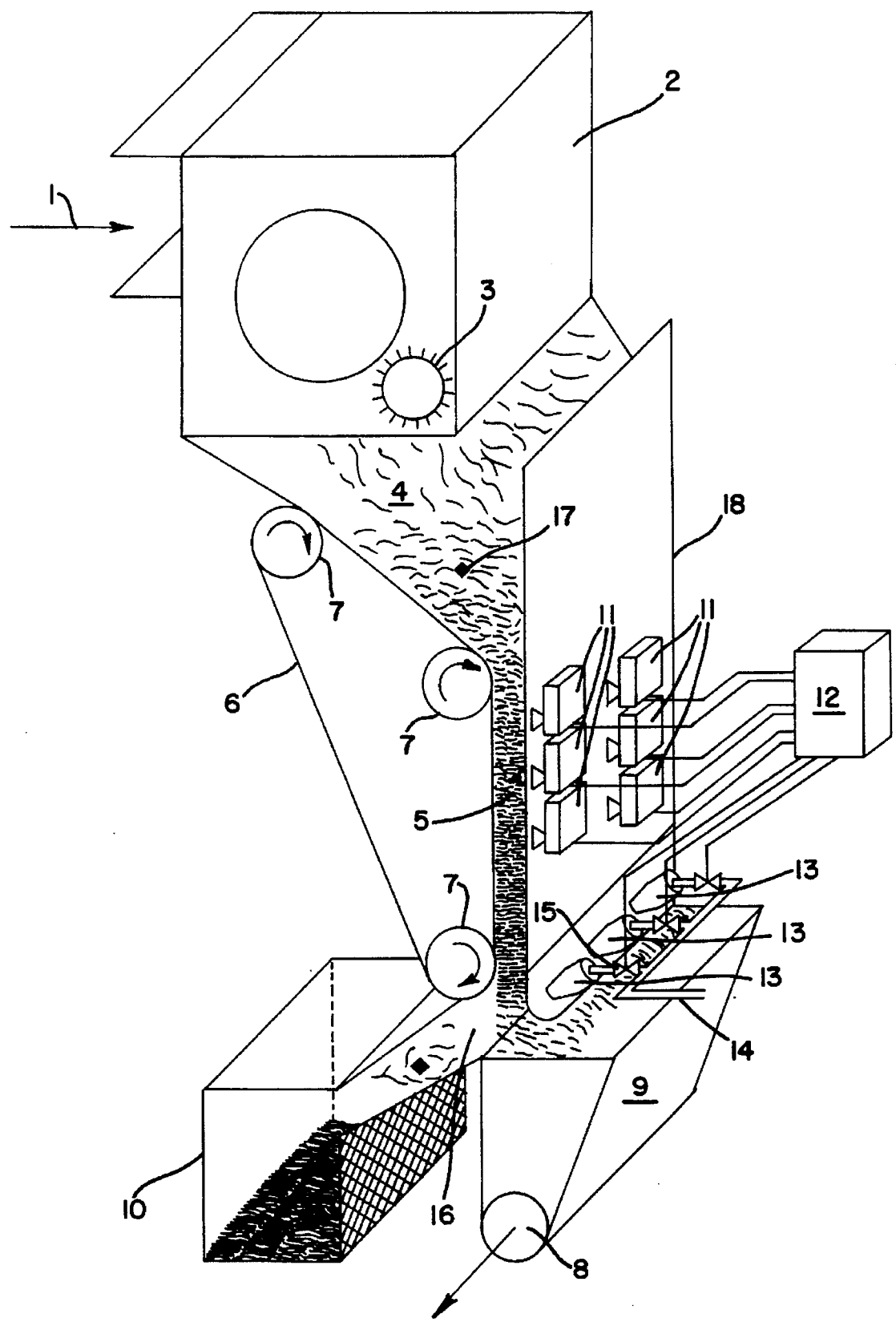

PROCESS FOR THE RAPID RECOGNITION AND FILTERING OUT OF DIFFERENTLY COLORED FOREIGN BODIES IN FIBER PROCESSING LINES

The cotton processing industry suffers considerable quality defects and machinery malfunctions as a result of the presence of foreign bodies in the flow of fibres such as, for example, parts of packagings and residues of fabrics.

A known process for the recognition and removal of foreign bodies is to place directly on the cutting head a camera which, when foreign elements are detected, deliver signals to a switching station, whereafter the flow of fibres is deflected. In that method, problems arise mainly due to the varying surface of the bales for cutting and the resulting imprecision of the signals.

In another process the fibres are allowed to run into a shaft and stand still therein. Then a camera observes the column and removes the contents of the shaft if foreign bodies are present. That method does not allow a continuous flow of fibres, a considerable quantity whereof being separated if even only one foreign body is detected. Due to the long evaluation time for the large quantity of data, with that process it is possible to obtain only throughputs which are inadequate from any production lines.

The present invention enables foreign bodies to be recognized and purposefully filtered out with continuous operation and high throughputs. According to the invention the color is recognized by color sensors which inspect the flow of fibres in a number of columns one beside the other.

An embodiment of the present invention is illustrated in the single drawing FIGURE.

The invention will be described with reference to the drawing. Fibres arriving from a bale cutter pass via a connecting member (1) into a condenser (2), whereafter they are poured unpressurized past a filtering out drum (3) into a funnel (4). The fibres are then compacted in a shaft (5). The shaft consists of a transparent sheet (18) and a conveyor belt (6). The conveyor belt is driven over rollers (7), thus compacting the fibres, which it guides along the sheet (18). Mounted on the other side of the sheet are color sensors (11), for example, Yamatake CS70-CA1. Since with said color sensors the portion to be observed (approximately 1 cm$^2$) is very small in comparison with the large quantities of fibres and moreover scanning and evaluation require a certain time cycle, the sensors are disposed in columns one beside the other. With large quantities of fibres, and therefore a high conveyor belt speed, the alternating operation of the evaluation cycle of the sensors in dependence on sensor position and belt speed ensures that the fibre mat can be substantially uniformly and sufficiently completely monitored.

Thus, for example, with an arrangement of 3 sensors one below the other (cf. the drawing), a foreign body will be detected by at least one of the 3 color sensors even at belt speeds which are faster than the response time of the sensors. The control system is so designed that a foreign body having a projected surface smaller than 1 cm$^2$ (depending on sensor data) is detected by only one sensor— i.e., the same fibre zones are not completely doubly checked. To create constant optical conditions, this portion is illuminated with constant light from the sensors (11). The reflected light is evaluated for its composition of the 3 basic colors and also as regards intensity and saturation. The assessment of the results as "satisfactory" or "poor" is performed by means of a "teach-in" in a control unit (12). In a "teach-in", prior to the operation of the installation, normal fibre material is sent through the shaft and the recognized color is stored as "satisfactory". If no foreign body is detected, the fibres pass through a chute (9) into a negative pressure line (8) and are removed by suction.

When the sensors (11) detect a color deviation, the control system (12) actuates with delay a valve (15) which actuates a compressed air nozzle (13). In this way the foreign body is purposefully filtered out with only a few fibres and conducted via a channel (16) into a box (10). Air for the compressed air nozzles (13) is supplied via a pneumatic line (14). The use of many sensors means that detection and evaluation take only a short time.

The arrangement described enables an apparatus to be obtained whose size is independent of the stream of fibres and which can therefore be used in a variable manner.

Due to the selective filtering out, very little fibre is lost with this process.

I claim:

1. A process for the recognition and filtering out of differently colored foreign bodies from fibre flocks in processing lines, said process including the steps of:

continuously transporting the fibres over a measuring distance and past a plurality of color sensors to detect the presence of said in bodies in the flocks; and compacting the fibres in a converging shaft, one wall of which is formed by a conveyor belt which moves the fibres along and past the color sensors;

the color sensors being disposed in columns one beside the other.

2. The process according to claim 1, including one to five columns of color sensors, each column having a solenoid which actuates a compressed air ejector nozzle in accordance with the signal of the associated color sensors.

3. The process according to claim 1, wherein each of the individual color sensors has its own illumination source incorporated therein for the inspection.

4. The process according to claim 1, wherein the color sensors are so operated that fibre zones smaller than 1 cm$^2$ are inspected by only one of two color sensors disposed one below the other as the fibre zones are conveyed past said two sensors.

5. The process according to claim 1, wherein the operation of the color sensors is adjusted so that the fibre zones which are inspected by the sensors do not completely register with one another.

6. The process according to claim 1, including a control system which actuates ejectors corresponding to the sensors, and the actuation of the ejectors is delayed in response to the transport speed of the fibres.

7. The process according to claim 6, including one to five columns of color sensors, each column having a solenoid which actuates a compressed air ejector nozzle in accordance with the signal of its associated color sensor.

8. A process for the recognition and filtering out of differently colored foreign bodies from fibre flocks in processing lines, said process including the steps of:

continuously transporting the fibres over a measuring distance and past a plurality of color sensors to detect the presence of said foreign bodies in the fibre flocks;

compacting the fibres in a converging shaft; and conveying the fibres along the color sensors by a single conveyor belt, the color sensors being disposed in columns one beside the other.

9. A process for the recognition and filtering out of differently colored foreign bodies from fibre flocks in processing lines, including the step of continuously transporting the fibres over a measuring distance and past a plurality of color sensors to detect the presence of the foreign bodies in the fibre flocks, the color sensors being disposed in columns one beside the other, and wherein each of the individual color sensors has its own illumination source incorporated therein for the inspection.

10. The process according to claim 9, wherein the color sensors are so operated that fibre zones smaller than 1 cm$^2$ are inspected by only one of two color sensors disposed one below the other as the fibre zones are conveyed past said two sensors.

11. The process according to claim 9, wherein the operation of the color sensors is adjusted so that the fibre zones which are inspected by the sensors do not completely register with one another.

12. The process according to claim 9, including a control system which actuates ejectors corresponding to the sensors, and the actuation of the ejectors is delayed in response to the transport speed of the fibres.

13. The process according to claim 9, including one to five columns of color sensors, each column having a solenoid which actuates a compressed air ejector nozzle in accordance with the signal of its associated color sensor.

* * * * *

UNITED STATES PATENT AND TRADEMARK OFFICE
CERTIFICATE OF CORRECTION

PATENT NO.   : 5,626,237
DATED        : May 6, 1997
INVENTOR(S)  : Hubert A. Hergeth It is certified that error appears in the above-indentified patent and that said Letters Patent is hereby corrected as shown below:

Col. 2, line 23, delete "said in bodies in the flocks" and insert
--said foreign bodies in the fibre flocks--.

Signed and Sealed this

Fourteenth Day of October, 1997

Attest:

BRUCE LEHMAN

Attesting Officer

Commissioner of Patents and Trademarks